US007509882B2

(12) United States Patent
Monteiro et al.

(10) Patent No.: US 7,509,882 B2
(45) Date of Patent: Mar. 31, 2009

(54) MULTIAXIAL UNIVERSAL TESTING MACHINE

(75) Inventors: João Luís Marques Pereira Monteiro, Guimarães (PT); Ana Maria Moreira Ferreira Da Rocha, Guimarães (PT); Mário Filipe Araújo Gonçalves Lima, Braga (PT); Júlio Manuel de Sousa Barreiros Martins, Braga (PT); Mário Duarte de Araújo, Braga (PT); Carlos Alberto Caridade Monteiro Couto, Braga (PT); Fernando Jorge De Castro Vieira Mendes, Braga (PT)

(73) Assignee: Universidade do Minho, Braga (PT)

( * ) Notice: Subject to any disclaimer, the term of this patent is extended or adjusted under 35 U.S.C. 154(b) by 0 days.

(21) Appl. No.: 10/575,867

(22) PCT Filed: Oct. 28, 2004

(86) PCT No.: PCT/PT2004/000026

§ 371 (c)(1),
(2), (4) Date: Jun. 26, 2007

(87) PCT Pub. No.: WO2005/040765

PCT Pub. Date: May 6, 2005

(65) Prior Publication Data

US 2008/0034885 A1 Feb. 14, 2008

(30) Foreign Application Priority Data

Oct. 28, 2003 (PT) ..................... 103034

(51) Int. Cl.
*G01D 7/00* (2006.01)
(52) U.S. Cl. ............................. 73/862.046
(58) Field of Classification Search ............ 73/862.046
See application file for complete search history.

(56) References Cited

U.S. PATENT DOCUMENTS 6,247,370 B1  6/2001  Ramaswamy et al.

(Continued)

FOREIGN PATENT DOCUMENTS

DE  36 17 455 A1  11/1987

(Continued)

OTHER PUBLICATIONS

G. T. Urumov, "A Machine for Testing Sheet Specimens for Fatigue Under Two-Frequency Loading Conditions", Industrial Laboratory (Diagnostics of Material), vol. 63, No. 10, Oct. 1997, pp. 620-622.

(Continued)

*Primary Examiner*—Harshad Patel
*Assistant Examiner*—Octavia Davis
(74) *Attorney, Agent, or Firm*—Sughrue Mion, PLLC

(57) ABSTRACT

The invention concerns a multiaxial universal testing machine, which allows evaluating the mechanical behavior and performance of materials with planar structures, such as fabrics, composites and laminates. The machine comprises 4 horizontal axes, each one with 2 arms, resulting in a final arrangement of 8 gripping jaws at 45°, displaceable along slide rails and moved by the action of 8 independent motors. The connection between a gripping jaw and its respective motor is assured by a linear actuator. The test specimen is fixed by the gripping jaws and can be subject to tensile, compression and fatigue testing, making possible the analysis of the materials behavior under simultaneous multi-directional loads.

8 Claims, 3 Drawing Sheets

U.S. PATENT DOCUMENTS 7,051,600 B1 * 5/2006 Cavallaro et al. ...... 73/862.041

FOREIGN PATENT DOCUMENTS

JP 11-327286 A 11/1999

OTHER PUBLICATIONS

J. P. Boehler, et al, "A New Direct Biaxial Testing Machine for Anisotropic Materials", Experimental Mechanics, Society for Experimental Stress Analysis, US, Mar. 1, 1994, pp. 1-9, XP000574645, ISSN: 0014-4851.

* cited by examiner

MULTIAXIAL UNIVERSAL TESTING MACHINE

BACKGROUND OF THE INVENTION

The present invention relates generally to universal testing machines and more specifically to methods for applying a multiaxial load to a planar test specimen. Actually, there is no equipment capable to evaluate some behaviour parameters, like tensile, compression or fatigue, in different directions simultaneously. As alternative, the evaluation of these characteristics has been done resorting to the unidirectional dynamometer, doing the assays only in one direction or successively in each direction. In this case the results don't give any indication about the interaction of the multiaxial forces.

In known testing machines of that kind, we observe a frame with an upper transverse member and a base transverse member as well as two interconnecting guide pillars in way to tensile compression and beading testing operations. A central transverse member is displaceable along the guide pillars, while testing devices can be connected between upper and base members and/or between central and base members. The central member is connected to cylinder bodies enclosing the guide pillars (UK Patent Application GB 2276949 A). Because the machine only has one axis, we only can perform uniaxial testing operations, which is the great disadvantage of this machine. Furthermore, only one member can be moved, while the others are static.

Others devices actually can perform biaxial testing operations. The Biaxial Testing Apparatus (U.S. Pat. No. 5,905, 205) concerns a rhombus-shaped four-bar linkage that is attached at one vertex to a fixed attachment point and a uniaxial tensile force is applied to the opposite vertex. The test specimen is placed inside the four-bar linkage and is attached to the four-bar linkage by load transfer members connected at one end to the links of the four-bar linkage and at their other end to the gripping jaws holding the testing specimen. The application of the uniaxial tensile force then produces a biaxial tensile force in the test specimen. The particular disadvantage of this approach is the restriction imposed by the physical structure of the device, hindering others testing configurations for beyond the biaxial testing.

SUMMARY OF THE INVENTION

In accordance with the foregoing principles and objects of the present invention, a novel machine and method for applying a multiaxial stress is described. The idea of this invention is based on the evaluation of the mechanical behaviour and performance of materials with planar structures under simultaneous multi-directional loads, with a wide variety of operation combinations.

The TexTest™ equipment comprises an octagonal prismatic central block, working as a supporting structure, where 8 platforms are rigidly attached in a radial orientation. Each platform is the bed for an "arm", responsible for applying a force and displacement to one of the 8 jaws where the specimen is attached. Each one of these 8 "arms" is made up of an electric actuator with speed reducer, coupled to a linear drive, in series with a load cell and a gripping jaw.

The rotational movement of the motor is converted into linear displacement of the jaw. The geared motor is responsible for low speed rotary motion and high torque, which is turned into linear displacement and force applied to the jaw. The main advantage of this mechanical solution is an overall axial alignment of the linear drive with the applied force, thus eliminating any undesirable bending moments. Furthermore the motor is equipped with a rotational encoder which gives the information to the electronic drive about the rotor position counting the number of rotations. With this information is possible to control accurately the rotor position and consequently the respective gripping jaw displacement.

The load cell is the transducer that converts the physical value of the force applied to test specimen into an electric signal that can be digitalised and acquired by the data acquisition system incorporated in the computer controlled system. As it can only work under uni-axial stress, a pivoted coupling was provided.

The jaw is responsible for grabbing the test specimen by friction, therefore eliminating any slipping from the jaw. The gripping load is applied by a manually driven screw handle, therefore simplifying the design and eliminating any need for pneumatic pressure or complex and heavy electric actuators. In the interest of cleanliness, hydraulics has always been ruled out.

A slide carriage supports each jaw that can travel along a linear dry bearing, responsible for the correct alignment of the test specimen displacement.

The interface between the machine and the operator is done by a PC, working with specific software developed by the research team. This software comprises a set of menus to guide the user in an objective way, showing him, step by step, the different options he can take. The user program can be divided in four parts: configuration, monitoring, results and calibration. Thus, the program allows the configuration of new assays (or gets stored assays) and the real time visualization of parameters evolution during the assay. All the testing results are presented in a graphical mode and the values of the measured force, elongation and extension characteristics are also depicted. These results are also available on a report sheet that includes data regarding testing machine settings (pre-load, testing speed, gauge, elongation and force ranges) and identification headers. The statistical treatment of data results is also provided by the program, including it on the report sheets. However, these results can also be treated using other statistical software tools.

BRIEF DESCRIPTION OF THE DRAWINGS

The present invention will be more clearly understood from a reading of the following detailed description in conjunction with the accompanying drawings wherein.

DETAILED DESCRIPTION

Figure 1:
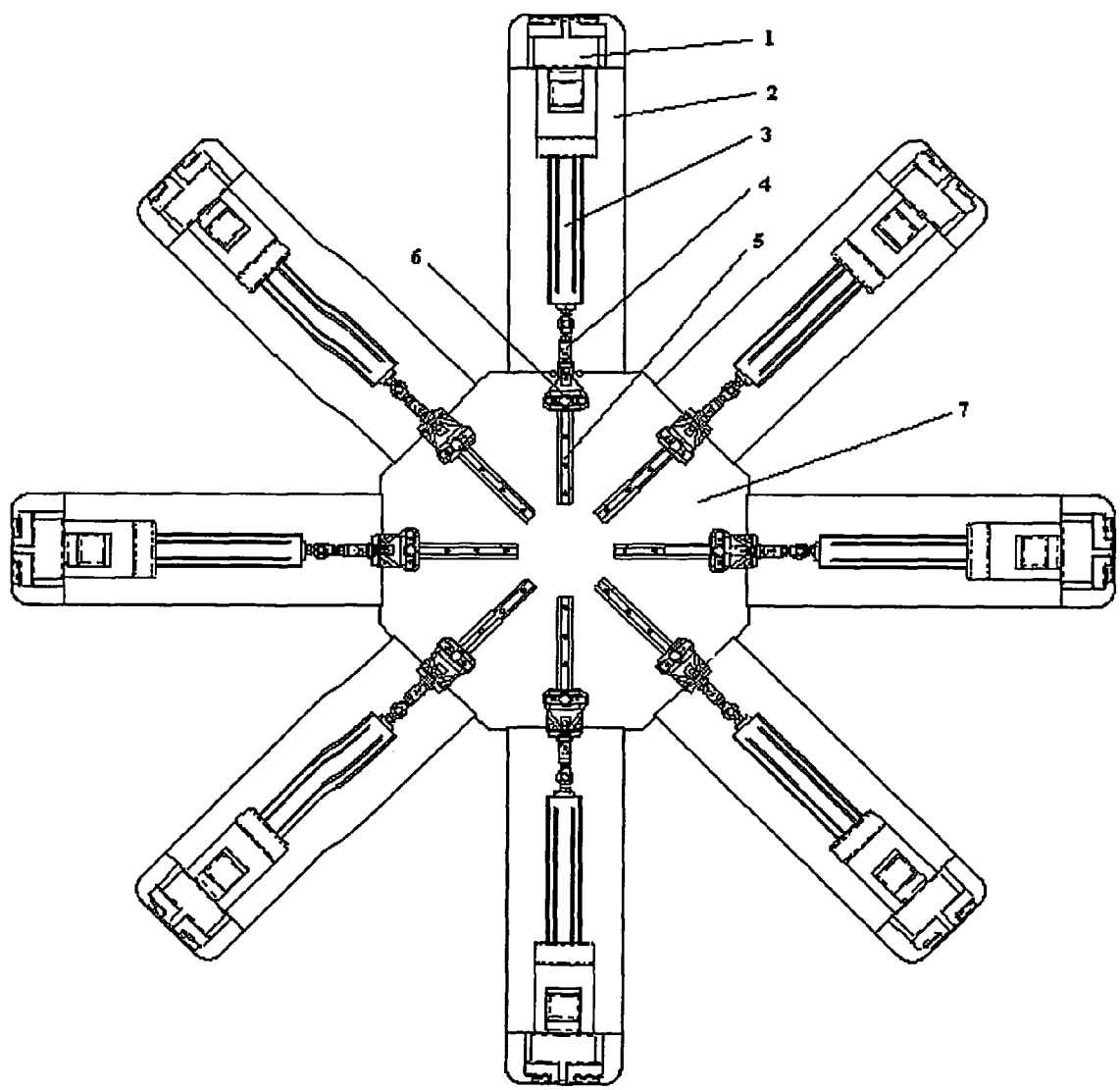
FIG. 1 is an upper view of the testing machine.

The testing machine shown in the drawings was designed to carry out a very wide range of different kinds of testing operators, such as for example tensile, compression or fatigue, on materials with planar structures, such as fabrics, composites and laminates.

Referring now to FIG. 1 of the drawings, there is shown a global upper view of the testing machine, where is evident the octagonal shape of the central block 7, due to the 8 mid-axis of the system, decreasing the encumbrance and making easier the operator access. This central block is the main support of the machine and where the flanges 2 are attached. The flanges 2 were designed to decrease the amount of material used in its construction and to make easier the access to the central area to placement of the test specimen.

Figure 2:
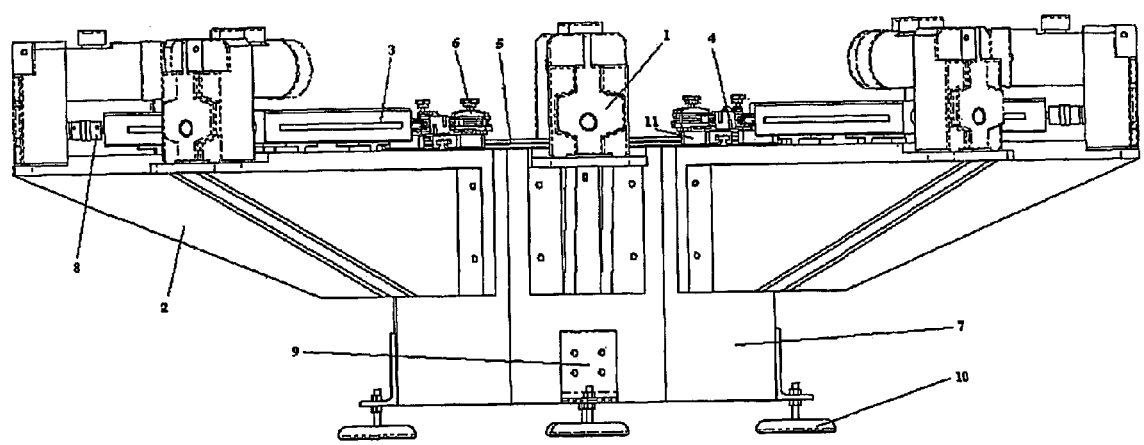
FIG. 2 is a side view of the testing machine.

FIG. 2 is a side view of the testing machine, showing another view of the central block 7, which is supported by 4 anti-vibration mounts 10 to regulate the machine leveling and to stabilize the central block 7. To attach the mounts 10 to the central block 7, angle steel 9 with standard dimensions are used.

Figure 3:
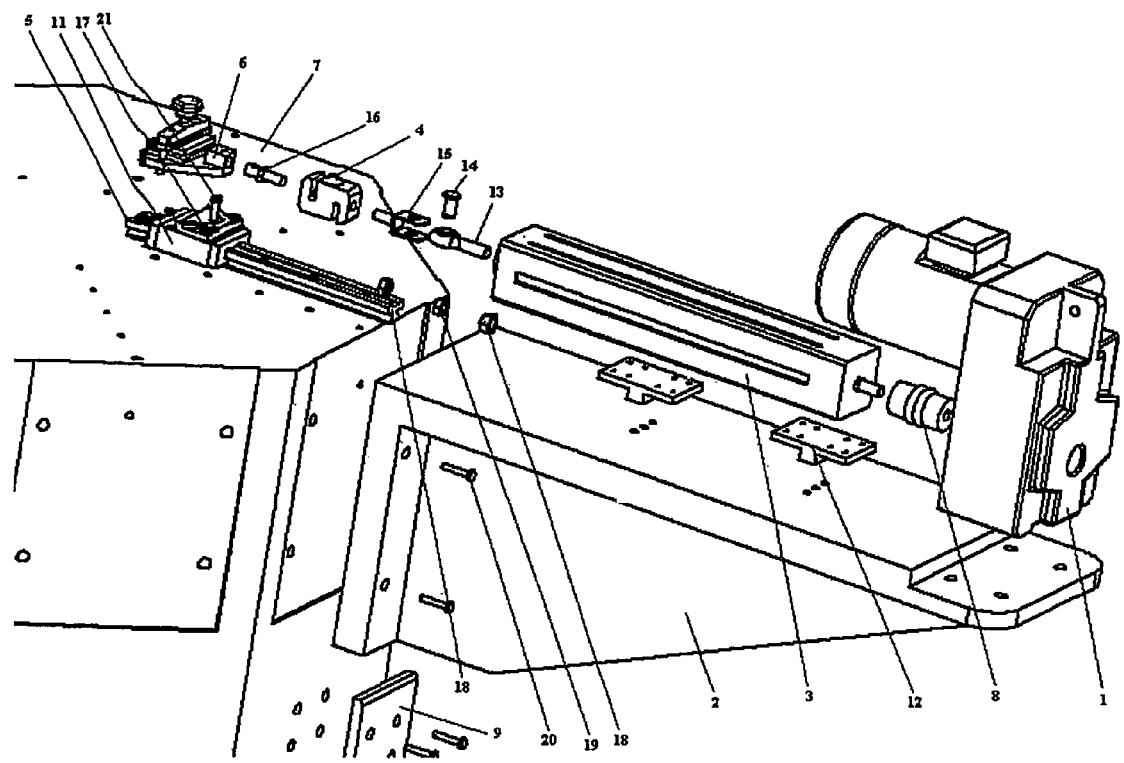
FIG. 3 is an exploited view from an "arm" of the testing machine. This image only shows one "arm" because the others have the same structure.

Referring to FIG. 3 it is possible to see an exploited view of one "arm" allowing a detailed observation of all components of the "arm". Each flange 2 functions as the basis of each "arm", supporting its components. An "arm" is composed firstly by a geared motor 1 to allow the necessary torque at low rotations. The connection between the geared motor 1 and the screw type linear drive 3 is done by spindles joint 8, selected considering the diameter and the maximum torque supported by the screw type linear drive. The screw type linear drive 3 is a mechanism to transform a rotational movement (from the motor) into a linear displacement (to the gripping jaw), so the displacement sense of the gripping jaw only depends of the sense rotation of the motor. The screw type linear drive 3 was chosen to get an axial alignment with the applied force, eliminating flectional moments. Its connection to the flange 2 is done by 2 supports 12, with the height necessary to keep the spindles alignment. On the other end of the screw type linear drive 3 it was placed an articulation head 13 linked to a clevis 15 by a stud 14. This set is used to minimize the negatives consequences of possible horizontal misalignments. The clevis 15 is prepared to connect to the load cell 4, which is responsible for converting the force value applied to test specimen in an electric value in order to be acquired and processed by the control system. The gripping jaw 6 is linked to the load cell 4 by an element 16 designed to fit correctly into the joined elements. The gripping jaw 6 is manually screwed and the teeth of the gripping jaw can be replaced by others with different shapes and different test specimen contact surfaces, specific to the test specimen material. The teeth, must generate sufficient friction with the test specimen, proportional to the screw force to impede any slipping. The gripping jaw 6 seats on a piece 17 designed to attach correctly the gripping jaw 6 to a non lubricated slide carriage 11, which moves on a slide rail 5. This set, composed by the slide carriage 11 and the slide rail 5, forms the guidance of the gripping jaw 6, driving it according to the "arm" direction.

As referred, all "arms" are independent from each other, meaning only certain arms are operated depending on the desired kind of assay. The placement of the test specimen is done by holding its extremities in the gripping jaw teeth. Obviously the test specimen shape must be defined according to the kind of assay to be performed.

All the assay configurations depend practically on the design of the control software, because the designed physical structure allows total freedom at this point.

The invention claimed is:

1. A multiaxial universal testing machine providing any of uni, bi, tri and tetra dimensional movement comprising:
    a central block 7, working as a supporting structure;
    eight platforms 2 rigidly attached in a radial orientation at 45° having four horizontal axes, each axis with two horizontal arms;
    wherein the eight horizontal arms are designed to apply a required force and displacement in a uni- bi, tri or tetra-axial orientation;
    eight pairs of gripping jaws for aftaching a test specimen with a shape adequate to the test type thereto;
    detecting means for independent monitoring and actuation of each arm;
    a control and management system for data acquisition and processing and for testing machine calibration and assay programming.

2. A multiaxial universal testing machine according to claim 1 wherein each of the platforms is a base, respectively, for each arm, and each arm is made up of an electric motor with speed reducer 1, coupled to a screw type linear drive 3, in series with a load cell 4 and a gripping jaw 6.

3. A multiaxial universal testing machine according to claim 2 the rotational movement of the motor 1 is converted into linear displacement and force by the screw type linear drive 3, monitoring and controlling this parameters with a rotary encoder in the motor 1 (to the displacement) and a load cell 4, between the screw type linear drive 3 and the gripping jaw 6 (to the force), respectively.

4. A multiaxial universal testing machine according to claim 3, wherein each gripping jaw 6 seats on a slide carriage 11 that can travel along a linear dry bearing 5, responsible for the correct alignment of the test specimen displacement.

5. A multiaxial universal testing machine according to claim 1, the multiaxial universal testing machine being operative along any of 1, 2, 3, or 4 axes (uni, bi, tri and tetra-axial), keeping all the capabilities needed to evaluate the mechanical behavior and performance of materials with planar structures.

6. A multiaxial universal testing machine according to claim 1 wherein the control system for machine supervision and management system for data acquisition and processing includes a central processing unit, a display for real-time visualization of command information (configuration, monitoring and calibration) and test results and a data storage and processing system.

7. A method for multiaxial testing of planar specimens comprising the steps of:
    providing eight platforms having four horizontal axes each with two horizontal arms;
    providing a test specimen being one of textiles, composites, and laminates;
    attaching the test specimen to gripping jaws involved in an assay to perform, according to the desired orientation;
    applying force to the test specimen through the displacement of the gripping jaws and following the configuration parameters defined to the test performance, including the kind of assay and the active axis,
    said applying force step including the step of independently monitoring and actuating each arm.

8. A method according to claim 7 wherein the kind of assay is one of tensile, compression and fatigue.

* * * * *